United States Patent [19]

Schmued

[11] Patent Number: 4,716,905

[45] Date of Patent: Jan. 5, 1988

[54] METHOD OF RETROGRADE FLUORESCENT LABELING OF NEURONS

[75] Inventor: Laurence C. Schmued, Irvine, Calif.

[73] Assignee: Fluorochrome, Inc., Englewood, Colo.

[21] Appl. No.: 780,100

[22] Filed: Sep. 25, 1985

[51] Int. Cl.$^4$ .............................................. A61B 5/05
[52] U.S. Cl. .................................. 128/654; 514/636; 424/9; 128/1 R
[58] Field of Search ............... 128/1 R, 654; 514/636; 424/2, 9

[56] References Cited

U.S. PATENT DOCUMENTS 2,510,047  5/1950  Ewins .

OTHER PUBLICATIONS

Murgatrayd 2 Hydroxystilbamidine Isethionate: A New Fluorochrome for Use in General Pathology in *Histochemistry*, 74(1), 1982, pp. 107–114.
L. C. Schmued, et al., SITS: A Covalently Bound Fluorescent Retrograde Tracer That Does Not Appear to be Taken Up by Fibers-of-Passage, Brain Research, 249, (1982), pp. 137–141.
M. Bentivolgio, et al., Fluorescent Retrograde Triple Labeling of Brainstem Reticular Neurons, Neuroscience Letters, 46, (1984), pp. 121–126.
H. G. J. M. Kuypers, et al., Retrograde Transport of Bisbenzimide and Propidium Iodide Through Azons to Their Parent Cell Bodies, Neuroscience Letters, 12, (1979), pp. 1–7.
M. Bentivoglio, et al., Fluorescent Retrograde Neuronal Labeling in Rat by Menas of Substances Binding Specifically to Adeninethymine Rich DNA, Neuroscience Letters, 12, (1979), pp. 235–240.
M. Bentivoglio, et al., Two New Fluorescent Retrograde Neuronal Tracers which are Transported Over Long Distances, Neuroscience Letters, 18, (1980), pp. 25–30.
M. Bentivoglio, et al., Retrograde Neuronal Labeling by Means of Bisbenzimide and Nuclear Yellow (Hoechst S 769121). Measures to Prevent Diffusion of the Tracers Out of Retrogradely Labeled Neurons, Neuroscience Letters, 18, (1980), pp. 19–24.
H. G. J. M. Kuypers, et al., Double Retrograde Neuronal Labeling Through Divergent Axon Collaterals, Using Two Fluorescent Tracers with the Same Excitation Wavelength which Label Different Features of the Cell, Brain Research, (1980), pp. 383–392.
K. Keizer, et al., Diamidino Yellow Dihydrochloride (KY-2HCl); New Fluorescent Retrograde Neuronal Tracer, Which Migrates Only Very Slowly Our of the Cell., Exp. Brain Research, 51, (1983), pp. 179–191.
L. C. Katz, et al., Fluorescent Latex Microspheres as a Retrograde Neuronal Marker for in Vivo and in Vitro Studies of Visual Cortex, Letters to Nature, vol. 310, Aug. 1984, pp. 498–500.

*Primary Examiner*—C. Fred Rosenbaum
*Assistant Examiner*—Jerome R. Smith, Jr.
*Attorney, Agent, or Firm*—Ralph F. Crandell

[57] ABSTRACT

A fluorescent retrograde axonal tracer method for use in neuroanatomical studies of the brain involves the use of dilute solutions of amidino-stilbene compounds or salts, specifically 2-hydroxy-4,4'-diamidinostilbene isethionate. The amidino stilbene tracer exhibits a high sensitivity and fluorescent intensity, retrogradely fills axons and dendrites extensively, is highly resistant to fading, is compatible with virtually all other histochemical procedures, and exhibits minimal uptake by fibers of passage. The method of using amidino stilbene or stilbamadine compounds involves injection of a dilute solution of the compound into the area of the brain to be studied. After a period of time, the tissue is examined under a fluorescence microscope.

7 Claims, No Drawings

METHOD OF RETROGRADE FLUORESCENT LABELING OF NEURONS

BACKGROUND OF THE INVENTION

1. Field of the Invention

The present invention relates to the use of fluorescent retrograde tracers to determine neuronal connectivity. More specifically, the present invention relates to the use of the compound 2-hydroxy-4,4'-diamidinostilbene isethionate for the retrograde axonal labeling of brain cells for determining their projections, axonal branching and chemical distribution patterns.

2. History of the Prior Art

Understanding the function of nervous tissue necessitates understanding its structure. One method which scientists and researchers utilize to understand the structure of the nervous system involves the injection of selected strains and dyes into specific areas of the brain. The pathways containing these indicators may be traced by observing the system under a fluorescence microscope. The nature of neural tissue has been studied by observing how nerve cells are connected to each other via long processes called axons. It is now known that certain substances, such as enzymes or dyes that are taken up by the axon terminals of cells and brought back to the cells by physiological cellular mechanisms, can be visualized in the cell body. For example, a substance can be injected into one area of tissue such as the brain, and by examining the tissue several days after that injection, the same substance can be observed in another area of the brain. Based on this observation, it is determined that transport has occurred and it can be concluded that one area of the brain connects to another area. Knowing those connections helps in understanding how the nervous system works.

One type of transport that has been studied involves injection of the enzyme horseradish peroxidase into terminal areas of neuronal axons in the brian, from which it is taken back in the axon to the parent neuronal cell bodies. This backwards transport is known as retrograde axonal transport. The procedure involves the use of the enzyme in a complex histochemical procedure involving reacting the tissue with certain chromogens, such as diamidino benzidine and tetramethyl benzidine, in the presence of the substrate hydrogen peroxide. The reaction produces a colored precipitate that can be visualized with a light microscope.

The next significant improvement came with the discovery that certain colored fluorescent compounds such as Dapi-Primuline, Evans Blue, and Propidium Iodine resulted in retrograde transport when injected into the brain. The transport was observable with a sensitive fluorescence microscope. With the colored dyes and a fluorescence microscope, the projections from one cell to different areas of the brain may be observed. That is, it may be determined if a cell gives rise to axons that go to one, two, or more separate areas in the brain. By injecting one dye into one part of the brain that contains an axon terminal, and another dye into a separate area, within a short period of time the brain sections may be cut and examined. If a cell contains the fluorescent dyes, it may be concluded that the cell connects to the brain areas into which the dyes were injected.

The foregoing techniques are limited by certain key problems. First, the dye taken up by the ends of the axons is often also taken up by fibers, known as fibers of passage, that happen to be passing through the area into which the dye is injected. In such a case, it is difficult to determine whether the process is retrogradely labeling cells that terminate in a given area, or is labeling cells because axons just jappened to be passing through the area going to another target area. Second, many of the dyed compounds are either toxic or are thought to be, or are, carcinogenic. Third, the compounds do not fluoresce brightly, or fade or degrade very rapidly. If the fluorophore (the fluorescent compound) fades rapidly, and before a picture can be taken, it becomes very difficult to get high quality photographs for analysis and publication. Fourth, most of the known compounds, after retrograde transport to the cell body, begin leaking out of the cells to nearby cells, resulting in a very confusing picture. Glial cells and neurons around the cells of interest are thus labeled, making it difficult to interpret the photographs. The problem is that the known dye compounds are not permanent or fast so as to remain within the cell. Fifth, the use of many of the particular dyes or fluorochromes is not compatible with other procedures because the dyes are washed out by solvents, their fluorescence is quenched by histochemical reagents, or they tend to fade too rapidly to be combined simultaneous with other procedures. Sixth, previously known fluorescent retrograde techniques have severe limitations because of the narrow ranges of permitted survival times of the animals after the injection. After injection, the dyes are brought back to the cell body at a specific unique rate. The time span between injection and analysis depends on the rate of transport, and is often very short. For example, the dye Nuclear Yellow requires a survival time of 18 hours after an injection of a 10 millileter axonal projection into the brain. If the survival time exceeds 24 hours, spurious results are obtained. If the survival time is less than 18 hours, no results are obtained because the dye does not reach the cell body in that time period. Presently known dyes have optimal survival time requirements within a very narrow range. In order to use two different colored dyes, either surgeries must be performed on different days, which jeopardizes the animal's life, or the dyes must be limited to those having the same exact survival time. A final limitation is that presently used retrograde tracers generally only label the nucleus or cytoplasm of a neuron, thus providing little information about the cytoarchitectronics (shape of the cell) of labeled cells.

A significant improvement in this technology occcurred when it was discovered that a stilbene derivative, 4, acetamido-4-isothiocyanostilbene2, 2'-disulphonic acid (SITS), could be used as a tracer, and was not taken up by fibers of passage (Schmued and Swanson, *Brain Research* 249 (1982) 137—141). The principal problem with the SITS compound was that it apparently included a mixed group of uncharacterized chemicals that varied from batch to batch and from manufacturer to manufacturer. Often, retrograde labeling was not obtained at all, depending on the SITS batch employed. Consistently reproducible results have not been obtainable with SITS.

OBJECTS AND SUMMARY OF THE INVENTION

It is the principal object of the present invention to provide an improved retrograde axonal tracer for use in the study of brain cells and processes relating thereto.

Another object of the present invention is to provide an improved retrograde tracer which is resistant to being taken up by fibers of passage.

A further object of the present invention is to provide an improved retrograde tracer which fluoresces brightly, has a long life, is resistant to leaking from the labeled cell, is compatible with other procedures, histochemical reagents and tracers, and extensively fills neuronal processes.

In accordance with the foregoing objects, the present invention comprises the discovery that an amidino stilbene salt, specifically 2-hydroxy-4,4'-diamidinostilbene isethionate is uniquely effective as a retrograde axonal tracer.

It is believed that amidino-stilbene salts, and more specifically, 4,4'-diamidinostilbene salts, and still more specifically, 2-hydroxy-4,4'-diamidinostilbene salts are effective as axonal retrograde tracers.

DESCRIPTION OF THE PREFERRED EMBODIMENT

In accordance with the present invention, it has been discovered that the fluorescent stilbene amidino derivative 2-hydroxy-4, 4'-diamidinostilbene isethionate, having the formula:

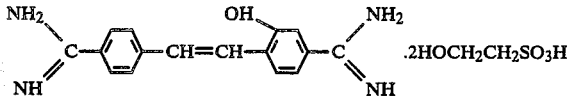

also known as hydroxystilbamidene isethionate, in dilute aqueous, phosphate buffer, or saline solution, is a highly effective retrograde axonal tracer. The compound is a fluorescent amidino-stilbene salt, more specifically a 4,4'-diamidinostilbene salt, such as the 2-hydroxy-4,4'-diamidinostilbene salt. The compound 2-hydroxy-4,4'-diamidinostilbene isethionate is a known trypanocidal compound, and is disclosed in U.S. Pat. No. 2,510,047, issued May 30, 1950, to A. J. Ewins for "Diamidine of 2-Hydroxystilbene." The disclosure of U.S. Pat. No. 2,510,047 is incorporatd herein by this reference and made a part hereof.

The fluorescent amidino stilbene compound is preferably stored in the dark at 4° C., either in the powder or the solution form. The storage temperature may range from below zero to about 60° C. Ambient room light is not detrimental, but direct sunlight should be avoided.

The compound is used in either aqueous, saline, or buffer solutions, in a concentration generally ranging from less than 1% to about 10%. The solvent is either distilled water or a 0.9% aqueous saline solution, or 0.2M ph 7.4 phosphate buffer. To form the solution, the compound is dissolved by agitation, such as by sonication or by vortexing, or by any appropriate method which will dissolve it into a solution or suspension. It may also be mixed in a phosphate buffer or ringers solution.

The amidino silbene compound can be used in solution concentrations ranging from about 1% to 10% depending on the desired procedure to be used. The higher the concentration, that is from about 5% to 10%, the more vibrant the labeling. The higher concentration also causes a degree of necrosis or lesion at the injection site. Generally, the preferred concentration is in the range of about 2%. For some tests, a pure crystal of the compound may be injected or placed on brain tissue. The compound may be placed on a gel foam and then injected by slow diffusion. A pump may be used to inject the solution either by constant delivery or cyclic delivery.

There are many ways of applying the tracer solution to the central and periphery nervous system and organ systems. One of the standard ways is by an iontrophoresis process in which electrical current of from about 1 to 10 microamps positive current, is pulsed over a ten minute interval. Alternatively, pressure injection using a microsyringe or an hydrualic pump may be utilized. The volumes used for pressure injections are usually in the range of about 0.02 to about 1 microliter, 0.1 ml being typical, delivered over about a ten minute interval.

The solution may be injected into the heart or into the lateral ventricles of the brain, from which it proceeds to the brain. It may also be injected into the retina of an eye. For general use in the central nervous system, volumes of 0.02 to 1 microliter would be prepared. For peripheral use, the volume may be increased.

A major advantage of the hydroxy amidino stilbene salt is its utility over a wide range of survival periods. It does not leak out of the cell even during long survival times. for shorter survival periods, such as one or two days, axonal labeling is observed, along with granular labeling within he cytoplasm. With medium survival times, ranging from three to five days, and long survival times of several weeks, the granules collect or "pile up" within the cell body because there are so many of the small vesicles and secondary lysosomes. With longer survival periods, the compound spreads to fill the dendrites to produce a striking conspicuous visual image. Usually three days are sufficient to achieve dendritic filling, although longer survival times, e.g., several weeks, produce an even more extensive neuronal filling. The hydroxy amidino stilbene compound has been observed within the cell, even after 30 days, and at that time was still within the cell, was bright, and had not leaked out to adjacent cells.

After injection of the solution of the hydroxy amidino stilbene into the desired area of the animal, such as in the brain, the animal, following anesthetic overdose, is preferably perfused with a variety of fixatives. While it is not necessary to fix the tissue, that is the fresh brain may be cut and examined, fixation is desirable to achieve some permanence of the tissue. To fix the tissue, a fixative compound is made up of 10% of a formalin solution, which itself is 37% formaldehyde, 20% of a 0.1 molar pH=7.4 phosphate buffer, and 70% of the 1% sodium chloride solution, and is injected into the animal. For immunocytochemical works, receptor autoradiography, or tissue that might be subsequently processed for either HRP or electron microscopy, a fixative is prepared by mixing 100 ml. of 0.1 molar, pH=7.4 phosphate buffer, 0.9 grams of sodium chloride, 4 grams of paraformaldehyde and 0.1 ml. of glutaraldehyde, and heating the solution to 60° C., until the paraformaldehyde goes into the solution. The solution is then cooled to room temperature. Five hundred milliliters of either fixative is pumped through the vascular system of the animal with the descending aorta clamped following anesthetic overdose. The tissue is then postfixed in the same fixative, but with 20% sucrose added, for 24 hours. At this point, sections can be cut into a variety of thicknesses for examination.

Thicker sections facilitate study of the dendritic arborizations, but also make it more difficult to photograph because of the increased depth of field in the microscope. The tissue may also be processed for paraffin or plastic embedding. Typically, the cut sections are mounted on glass slides, air dried and then cover-slipped, using either buffered glycerine or a non-fluorescing plastic polymer such as DPX. Sections cleared a few minutes in xylene and cover-shipped with DPX show best contrast and resolution. Counter-stains, such as ethidium bromide, may be used.

The brian cell structure may be studied and photographed with an epifluorescence microscope or any kind of fluorescence microscope, so long as it is equipped with a filter system whereby it may be excited with either ulraviolet or violet light. The injection site can then be studied, including the various processes extending from it, and the point of entry into the cells. The site can then be mapped out and photographed with either black and white or color film, to produce pictures which are suitable for further study and publication.

While a certain illustrative embodiment of the invention has been described above in considerable detail, it should be understood that there is no intention to limit the invention to the specific embodiment disclosed. On the contrary, the intention is to cover all modifications, alternatives, equivalents and uses falling within the spirit and scope of the invention as expressed in the appended claims.

What is claimed is:

1. The method of retrograde axonal tracing by the fluorescent labeling of neurons via axonal pathways to parent cell bodies in living tissue comprising injecting into live brain tissue to be labeled, the compound 2-hydroxy-4,4'-diamidinostilbene isethionate as a RAT in a concentration of between 1 and about 10% in the solvent selected from the group consisting of distilled water, 0.9% saline solution and a pH=7.4 phosphate buffer and waiting for a period of time after injection sufficient to label cells for subsequent examination under a fluorescene microscope.

2. The method of retrograde axonal tracing by the fluorescent labeling of neurons through retrograde axonal pathways to parent cell bodies in living tissue. comprising injecting into live brain tissue to be labeled a fluorescent hydroxy diamidinostilbene isethionate compound as a RAT.

3. The method defined in claim 2 wherein said fluorescent compound comprises 2-hydroxy-4,4'-diamidinostilbene isethionate.

4. The method defined in claim 2 wherein said fluorescent compound is in a concentration of between about 1 and about 10% by weight in distilled water.

5. The method defined in claim 2 wherein said fluorescent compound is in a concentration of between about 1 and about 10% by weight in a 0.9% aqueous saline solution.

6. The method defined in claim 2 wherein said fluorescent compound is in a concentration of between about 1 and about 10% by weight in a phosphate buffer solution.

7. The method of studying brain cells by injecting into the live brain tissue as a retrograde axonal tracer the fluorescent compound 2-hydroxy-4,4'-diamidino stilbene isethionate and, after a time sufficient for the retrograde axonal tracing of brain cells, examining the brain and the traced cells therein.

* * * * *